(12) United States Patent
Yoneda et al.

(10) Patent No.: US 10,486,491 B2
(45) Date of Patent: Nov. 26, 2019

(54) METHOD FOR ESTIMATING THERMAL SENSATION, THERMAL SENSATION ESTIMATION APPARATUS, AIR CONDITIONER, AND RECORDING MEDIUM

(71) Applicant: Panasonic Corporation, Osaka (JP)

(72) Inventors: Aki Yoneda, Hyogo (JP); Koichi Kusukame, Nara (JP); Hiroko Kubo, Nara (JP)

(73) Assignee: PANASONIC CORPORATION, Osaka (JP)

( * ) Notice: Subject to any disclaimer, the term of this patent is extended or adjusted under 35 U.S.C. 154(b) by 279 days.

(21) Appl. No.: 15/603,496

(22) Filed: May 24, 2017

(65) Prior Publication Data

US 2017/0341485 A1 Nov. 30, 2017

(30) Foreign Application Priority Data

May 31, 2016 (JP) .................................. 2016-109588
Dec. 15, 2016 (JP) .................................. 2016-243585

(51) Int. Cl.
| | | |
|---|---|---|
| *B60H 1/00* | (2006.01) | |
| *A61B 5/01* | (2006.01) | |
| *A61B 5/00* | (2006.01) | |
| *F24F 120/10* | (2018.01) | |

(52) U.S. Cl.
CPC ....... *B60H 1/00742* (2013.01); *A61B 5/0075* (2013.01); *A61B 5/0077* (2013.01); *A61B 5/015* (2013.01); *A61B 5/6893* (2013.01); *B60H 1/00792* (2013.01); *A61B 2576/00* (2013.01); *F24F 2120/10* (2018.01)

(58) Field of Classification Search
CPC ............ B60H 1/00742; B60H 1/00792; B60H 1/00285; B60H 1/00292; F24F 2120/10; F24F 2120/12; F24F 2120/14
See application file for complete search history.

(56) References Cited

U.S. PATENT DOCUMENTS

2015/0105976 A1\* 4/2015 Shikii ................... G06F 3/0488
701/36

FOREIGN PATENT DOCUMENTS

WO 2015/122201 8/2015

\* cited by examiner

*Primary Examiner* — Edward F Landrum
*Assistant Examiner* — Daniel C Comings
(74) *Attorney, Agent, or Firm* — Greenblum & Bernstein, P.L.C.

(57) ABSTRACT

A method for estimating thermal sensation calculates, on the basis of a thermal image, a first temperature, which is a surface temperature of a first area, and a second temperature, which is a surface temperature of a second area, calculates a first amount of heat lost on the basis of the first temperature and first information, calculating a second amount of heat lost on the basis of the second temperature and second information, obtains an area ratio of the first area to the second area, calculates a total amount of heat lost, which is an amount of heat lost from a whole body of a person in a unit area, on the basis of the first amount of heat lost, the second amount of heat lost, and the area ratio, and estimates thermal sensation, which indicates a degree of warmth or coldness of the person, on the basis of the total amount of heat lost.

29 Claims, 7 Drawing Sheets

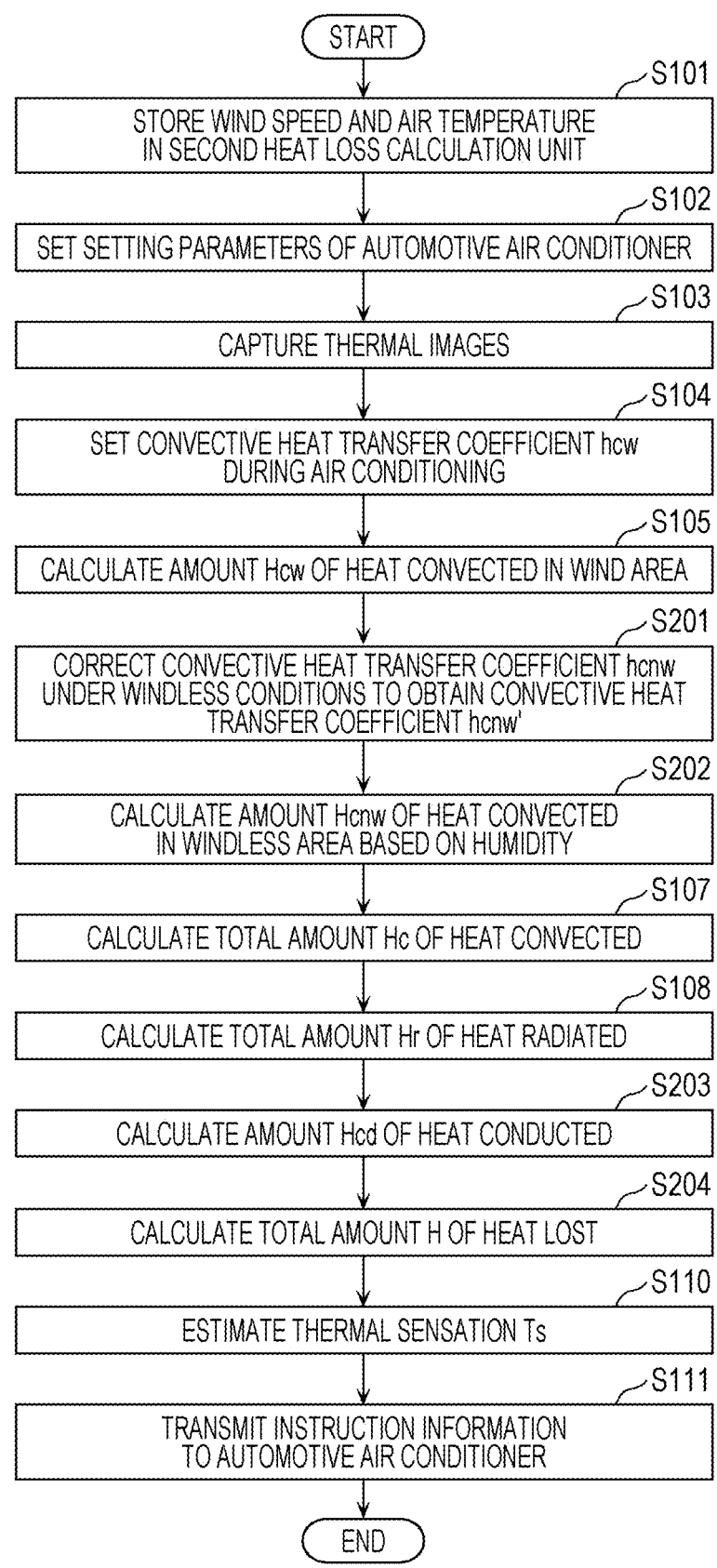

METHOD FOR ESTIMATING THERMAL SENSATION, THERMAL SENSATION ESTIMATION APPARATUS, AIR CONDITIONER, AND RECORDING MEDIUM

BACKGROUND

1. Technical Field

The present disclosure relates to a method for estimating thermal sensation, a thermal sensation estimation apparatus, an air conditioner, and a recording medium.

2. Description of the Related Art

A thermal sensation estimation apparatus that estimates thermal sensation, which indicates a degree of warmth or coldness of a person, without a report from the person is known. When the thermal sensation estimation apparatus is installed in an automobile, for example, an automotive air conditioner can be efficiently operated by controlling air temperature of the automotive air conditioner or the like on the basis of the estimated thermal sensation.

One of thermal sensation estimation apparatuses in examples of the related art is one that estimates thermal sensation by measuring an average skin temperature of a person on the basis of a fact that the average skin temperature and the thermal sensation have a high correlation. When this kind of thermal sensation estimation apparatus is used, however, a temperature sensor needs to be directly attached to a person's skin, which is not practical.

In order to solve the above problem, a thermal sensation estimation apparatus that focuses upon the amount of heat lost to an outside from a person's skin through clothes has been proposed (e.g., refer to International Publication No. 2015/122201). The thermal sensation estimation apparatus according to International Publication No. 2015/122201 calculates the amount of heat lost from a person on the basis of a difference between a human body surface temperature measured by a thermal camera and an atmospheric temperature (air temperature) and estimates thermal sensation on the basis of the calculated amount of heat lost from the person.

SUMMARY

In one general aspect, the techniques disclosed here feature a method for estimating thermal sensation used by a thermal sensation estimation apparatus. The method includes obtaining a thermal image of an area including a person captured by a thermal camera, calculating, on the basis of the thermal image, a first temperature, which is a surface temperature of a first area, which is a part of a human body surface area including skin or clothes of the person, exposed to a first thermal environment, and a second temperature, which is a surface temperature of a second area, which is at least a part of the human body surface area other than the first area, exposed to a second thermal environment different from the first thermal environment, calculating a first amount of heat lost, which is an amount of heat lost from the first area of the person in a unit area, on the basis of the first temperature and first information indicating thermal characteristics of the first thermal environment, calculating a second amount of heat lost, which is an amount of heat lost from the second area of the person in a unit area, on the basis of the second temperature and second information indicating thermal characteristics of the second thermal environment, obtaining an area ratio of the first area to the second area, calculating a total amount of heat lost, which is an amount of heat lost from a whole body of the person in a unit area, on the basis of the first amount of heat lost, the second amount of heat lost, and the area ratio, and estimating thermal sensation, which indicates a degree of warmth or coldness of the person, on the basis of the total amount of heat lost.

With the method for estimating thermal sensation according to the aspect of the present disclosure, thermal sensation can be accurately estimated even in a non-uniform thermal environment.

It should be noted that general or specific aspects may be implemented as a system, a method, an integrated circuit, a computer program, a computer-readable recording medium such as a compact disc read-only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7 is a flowchart illustrating a procedure of the operation of the thermal sensation estimation apparatus according to the second embodiment.

DETAILED DESCRIPTION

Figure 1:
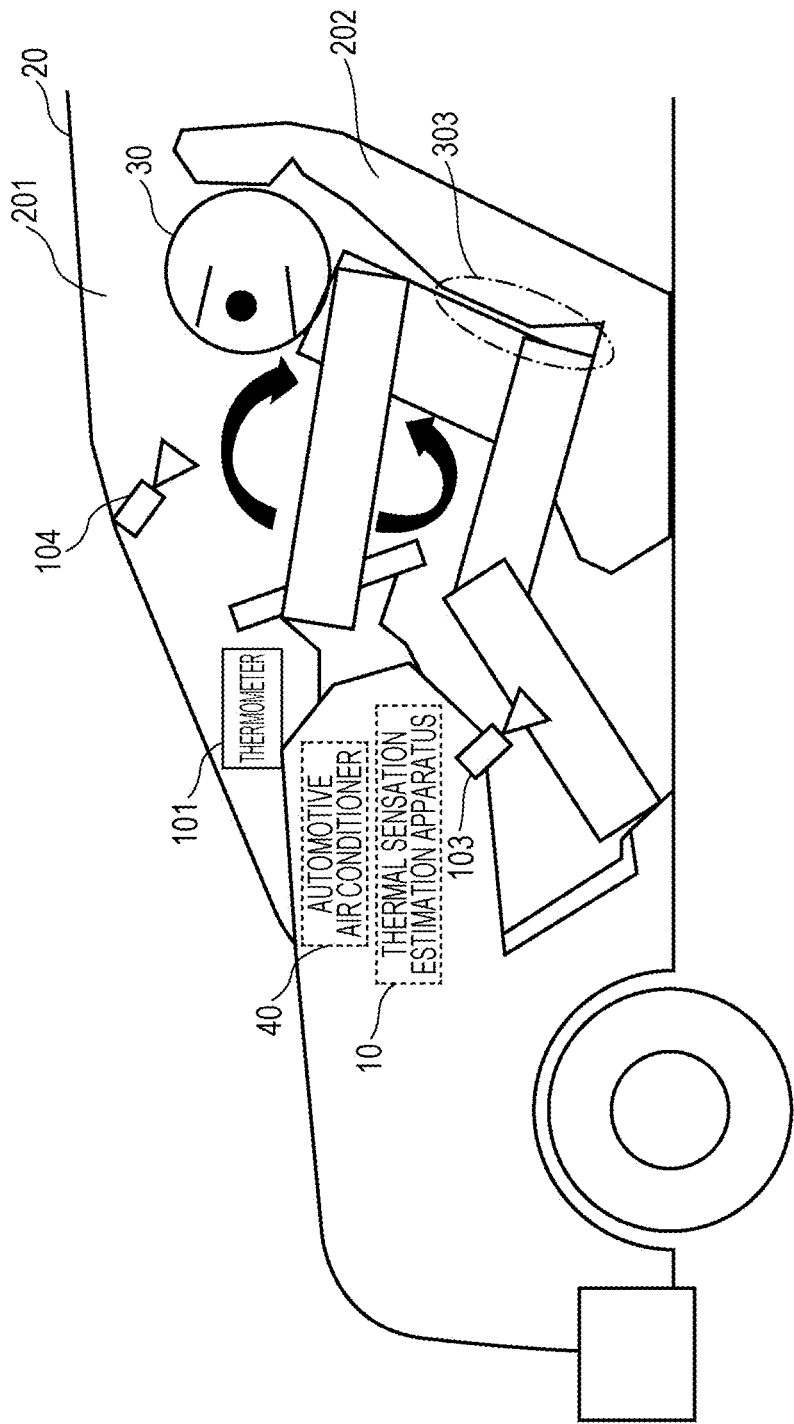
FIG. 1 is a diagram illustrating a use case of a thermal sensation estimation apparatus according to a first embodiment.

Underlying Knowledge Forming Basis of Present Disclosure

A method for estimating thermal sensation used by a thermal sensation estimation apparatus according to International Publication No. 2015/122201 presupposes that a thermal environment (atmospheric temperature) is uniform. If a thermal environment is not uniform due to cold or warm wind from an automotive air conditioner, heat from a seat heater, or the like as in an automobile, for example, thermal sensation is not accurately estimated.

The present disclosure, therefore, provides a method for estimating thermal sensation, a thermal sensation estimation apparatus, an air conditioner, and a recording medium capable of accurately estimating thermal sensation even in a non-uniform thermal environment.

A method for estimating thermal sensation according to an aspect of the present disclosure is a method used by a thermal sensation estimation apparatus. The method includes obtaining a thermal image of an area including the person captured by a thermal camera, calculating, on the basis of the thermal image, a first temperature, which is a surface temperature of a first area, which is a part of a human body surface area including skin or clothes of the person, exposed to a first thermal environment, and a second temperature, which is a surface temperature of a second area, which is at least a part of the human body surface area other than the first area, exposed to a second thermal environment different from the first thermal environment, calculating a first amount of heat lost, which is an amount of heat lost from the first area of the person in a unit area, on the basis of the first temperature and first information indicating thermal characteristics of the first thermal environment, calculating a second amount of heat lost, which is an amount of heat lost from the second area of the person in a unit area, on the basis of the second temperature and second information indicating thermal characteristics of the second thermal environment, obtaining an area ratio of the first area to the second area, calculating a total amount of heat lost, which is an amount of heat lost from a whole body of the person in a unit area, on the basis of the first amount of heat lost, the second amount of heat lost, and the area ratio, and estimating thermal sensation, which indicates a degree of warmth or coldness of the person, on the basis of the total amount of heat lost.

According to this aspect, when the first area and the second area of a human body surface area are exposed to the first thermal environment and the second thermal environment, respectively, the first amount of heat lost and the second amount of heat lost are calculated in the first area and the second area, respectively, and the total amount of heat lost is calculated by combining the first amount of heat lost and the second amount of heat lost using an area ratio. Furthermore, thermal sensation is estimated on the basis of the total amount of heat lost calculated in this manner. That is, since the total amount of heat lost is calculated in consideration of the human body surface area exposed to a non-uniform thermal environment, thermal sensation can be accurately estimated even if a person is in a non-uniform thermal environment.

For example, the first area may include at least a part of the human body surface area not exposed to air from an air conditioner. The second area may include at least a part of the human body surface area exposed to the air from the air conditioner.

According to this aspect, thermal sensation can be accurately estimated even in a thermal environment that is non-uniform due to air from an air conditioner.

For example, the total amount of heat lost may be calculated by weight-averaging the first amount of heat lost and the second amount of heat lost using the area ratio.

According to this aspect, the total amount of heat lost can be accurately calculated by weight-averaging the first amount of heat lost and the second amount of heat lost using an area ratio.

For example, the area ratio may be calculated on the basis of an area of the first area and an area of the second area in the thermal image.

According to this aspect, an area ratio can be easily calculated on the basis of areas of the first area and the second area in a thermal image.

For example, the area ratio may be calculated on the basis of a temperature histogram of the thermal image.

According to this aspect, an area ratio can be easily calculated on the basis of a temperature histogram of a thermal image.

For example, the area ratio may be a preset value.

According to this aspect, an area ratio can be easily obtained.

For example, the thermal camera may include a first thermal camera provided at a certain position and a second thermal camera provided at a position different from that of the first thermal camera. The thermal image may include a first thermal image captured by the first thermal camera and a second thermal image captured by the second thermal camera. The first area may be identified from the first thermal image. The second area may be identified from the second thermal image.

According to this aspect, by capturing the first thermal image and the second thermal image using the first thermal camera and the second thermal camera, respectively, the first area and the second area can be easily identified even if a human body surface area is relatively large.

For example, the person may be in contact with a certain member. An amount of heat transferred between the person and the certain member in a third area, which is a part of the human body surface area in which the person is in contact with the certain member, may be calculated on the basis of an amount of heat received by or lost from the certain member. An area ratio of the first area, the second area, and the third area may be obtained. The total amount of heat lost may be calculated on the basis of the first amount of heat lost, the second amount of heat lost, the amount of heat transferred, and the area ratio.

According to this aspect, the total amount of heat lost can be accurately calculated even if a person is in contact with a certain member.

For example, the certain member may be at least either a seat of a vehicle in which the person stays or a steering wheel. The amount of heat transferred may be an amount of heat transferred on a surface of the person's body at which the person is in contact with at least either the seat or the handle.

According to this aspect, the total amount of heat lost can be accurately calculated even if a person is in contact with a seat or a steering wheel.

For example, the amount of heat transferred may be measured by a thermometer provided for at least either the seat or the steering wheel.

According to this aspect, the amount of heat transferred can be easily measured using a thermometer.

For example, the amount of heat transferred may be measured by a heat flow meter provided for at least either the seat or the steering wheel.

According to this aspect, the amount of heat transferred can be easily measured using a heat flow meter.

For example, at least either the first information or the second information may include a temperature around the person.

According to this aspect, a temperature around a person can be used as at least either the first information or the second information.

For example, at least either the first amount of heat lost or the second amount of heat lost may be calculated by a calculation method in which a difference between the first temperature or the second temperature, whichever corresponds to the amount of heat lost, and the temperature is multiplied by a certain value.

According to this aspect, at least either the first amount of heat lost or the second amount of heat lost can be easily calculated.

For example, the temperature may be calculated on the basis of a thermal image representing temperature distribution in space.

According to this aspect, a temperature can be easily calculated on the basis of a thermal image.

For example, the temperature may be measured by a thermometer provided at a certain position around the person.

According to this aspect, a temperature can be easily measured using a thermometer.

For example, at least either the first information or the second information may include radiation temperature.

According to this aspect, radiation temperature can be used as at least either the first information or the second information.

For example, the radiation temperature may be calculated on the basis of a thermal image representing temperature distribution in space.

According to this aspect, radiation temperature can be easily calculated on the basis of a thermal image.

For example, at least either the first information or the second information may include wind speed and air temperature of wind around the person.

According to this aspect, wind speed and air temperature can be used as at least either the first information or the second information.

For example, a convective heat transfer coefficient between the human body surface area and at least either the first thermal environment or the second thermal environment may be set in accordance with the wind speed. At least either the first amount of heat lost or the second amount of heat lost may be calculated on the basis of the convective heat transfer coefficient, the air temperature, and the first temperature or the second temperature, whichever corresponds to the amount of heat lost.

According to this aspect, at least either the first amount of heat lost and the second amount of heat lost can be easily calculated.

For example, at least either the first amount of heat lost or the second amount of heat lost may be calculated by a calculation method in which a difference between the first temperature or the second temperature, whichever corresponds to the amount of heat lost, and the air temperature is multiplied by the convective heat transfer coefficient.

According to this aspect, at least either the first amount of heat lost or the second amount of heat lost can be easily calculated.

For example, the wind speed and the air temperature may be wind speed and air temperature of air from an air conditioner installed in space where the person stays.

According to this aspect, wind speed and air temperature of air from an air conditioner can be used as at least either the first information or the second information.

For example, the method may further include obtaining setting parameters of the air conditioner and calculating at least either the first amount of heat lost or the second amount of heat lost using the wind speed and the air temperature set using the setting parameters.

According to this aspect, wind speed and air temperature can be easily set using setting parameters of an air conditioner.

For example, the method may further include measuring in advance the wind speed and the air temperature at each position in the space for each pattern of the setting parameters of the air conditioner, estimating the wind speed and the air temperature in the human body surface area by identifying a position of the person in the space using the setting parameters of the air conditioner and the thermal image, and calculating at least either the first amount of heat lost and the second amount of heat lost using the estimated wind speed and air temperature.

According to this aspect, wind speed and air temperature can be easily estimated using setting parameters of an air conditioner and a thermal image.

For example, the first thermal environment and the second thermal environment may include humidity around the person.

According to this aspect, thermal sensation can be accurately estimated even if the first thermal environment and the second thermal environment include humidity.

For example, the method may further include outputting, to an air conditioner, instruction information for controlling air volume, air temperature, or wind direction of the air conditioner in accordance with the estimated thermal sensation.

According to this aspect, an air conditioner can be controlled such that, for example, thermal sensation becomes close to a value at which a person does not feel cold or hot. As a result, the air conditioner does not cool or heat too much, and power is saved.

For example, the thermal image may be captured inside a vehicle body of a vehicle in which the person stays.

According to this aspect, thermal sensation can be accurately estimated even in a non-uniform thermal environment such as an inside of a vehicle body of a vehicle in which a cooling operation is being performed in summer or a heating operation is being performed in winter.

A thermal sensation estimation apparatus according to an aspect of the present disclosure is a thermal sensation estimation apparatus. The thermal sensation estimation apparatus includes a processor and a memory. The processor performs operations including obtaining a thermal image of an area including a person captured by a thermal camera, calculating, on the basis of the thermal image, a first temperature, which is a surface temperature of a first area, which is a part of a human body surface area including skin or clothes of the person, exposed to a first thermal environment, and a second temperature, which is a surface temperature of a second area, which is at least a part of the human body surface area other than the first area, exposed to a second thermal environment different from the first thermal environment, calculating a first amount of heat lost, which is an amount of heat lost from the first area of the person in a unit area, on the basis of the first temperature and first information indicating thermal characteristics of the first thermal environment, calculating a second amount of heat lost, which is an amount of heat lost from the second area of the person in a unit area, on the basis of the second temperature and second information indicating thermal characteristics of the second thermal environment, obtaining an area ratio of the first area to the second area, calculating a total amount of heat lost, which is an amount of heat lost from a whole body of the person in a unit area, on the basis of the first amount of heat lost, the second amount of heat lost, and the area ratio, and estimating thermal sensation, which indicates a degree of warmth or coldness of the person, on the basis of the total amount of heat lost.

According to this aspect, when the first area and the second area of a human body surface area are exposed to the first thermal environment and the second thermal environment, respectively, the first amount of heat lost and the second amount of heat lost are calculated in the first area and the second area, respectively, and the total amount of heat lost is calculated by combining the first amount of heat lost and the second amount of heat lost using an area ratio. Furthermore, thermal sensation is estimated on the basis of the total amount of heat lost calculated in this manner. That is, since the total amount of heat lost is calculated in consideration of the human body surface area exposed to a non-uniform thermal environment, thermal sensation can be accurately estimated even if a person is in a non-uniform thermal environment.

An air conditioner according to an aspect of the present disclosure is an air conditioner including the above thermal sensation estimation apparatus. Air volume, air temperature, or wind direction is controlled on the basis of the thermal sensation estimated by the thermal sensation estimation apparatus.

According to this aspect, an air conditioner can be controlled such that, for example, thermal sensation becomes close to a value at which a person does not feel cold or hot. As a result, the air conditioner does not cool or heat too much, and power is saved.

A program according to an aspect of the present disclosure is a non-transitory recording medium storing a program for causing a computer to function as a thermal sensation estimation apparatus. The program causes the computer to perform operations including obtaining a thermal image of an area including a person captured by a thermal camera, calculating, on the basis of the thermal image, a first temperature, which is a surface temperature of a first area, which is a part of a human body surface area including skin or clothes of the person, exposed to a first thermal environment, and a second temperature, which is a surface temperature of a second area, which is at least a part of the human body surface area other than the first area, exposed to a second thermal environment different from the first thermal environment, calculating a first amount of heat lost, which is an amount of heat lost from the first area of the person in a unit area, on the basis of the first temperature and first information indicating thermal characteristics of the first thermal environment, calculating a second amount of heat lost, which is an amount of heat lost from the second area of the person in a unit area, on the basis of the second temperature and second information indicating thermal characteristics of the second thermal environment, obtaining an area ratio of the first area to the second area, calculating a total amount of heat lost, which is an amount of heat lost from a whole body of the person in a unit area, on the basis of the first amount of heat lost, the second amount of heat lost, and the area ratio, and estimating thermal sensation, which indicates a degree of warmth or coldness of the person, on the basis of the total amount of heat lost.

According to this aspect, when the first area and the second area of a human body surface area are exposed to the first thermal environment and the second thermal environment, respectively, the first amount of heat lost and the second amount of heat lost are calculated in the first area and the second area, respectively, and the total amount of heat lost is calculated by combining the first amount of heat lost and the second amount of heat lost using an area ratio. Furthermore, thermal sensation is estimated on the basis of the total amount of heat lost calculated in this manner. That is, since the total amount of heat lost is calculated in consideration of the human body surface area exposed to a non-uniform thermal environment, thermal sensation can be accurately estimated even if a person is in a non-uniform thermal environment.

It should be noted that these general or specific aspects may be implemented as a system, a method, an integrated circuit, a computer program, a computer-readable recording medium such as a compact disc read-only memory (CD-ROM), or any selective combination thereof.

Embodiments will be specifically described hereinafter with reference to the drawings.

The following embodiments are general or specific examples. Values, shapes, materials, components, arrangement positions and connection modes of the components, steps, the order of the steps, and the like mentioned in the following embodiments are examples, and do not limit the present disclosure. Among the components described in the following embodiments, ones not described in the independent claims, which define broadest concepts, will be described as arbitrary components.

First Embodiment 1-1. Configuration of Thermal Sensation Estimation Apparatus

Figure 2:
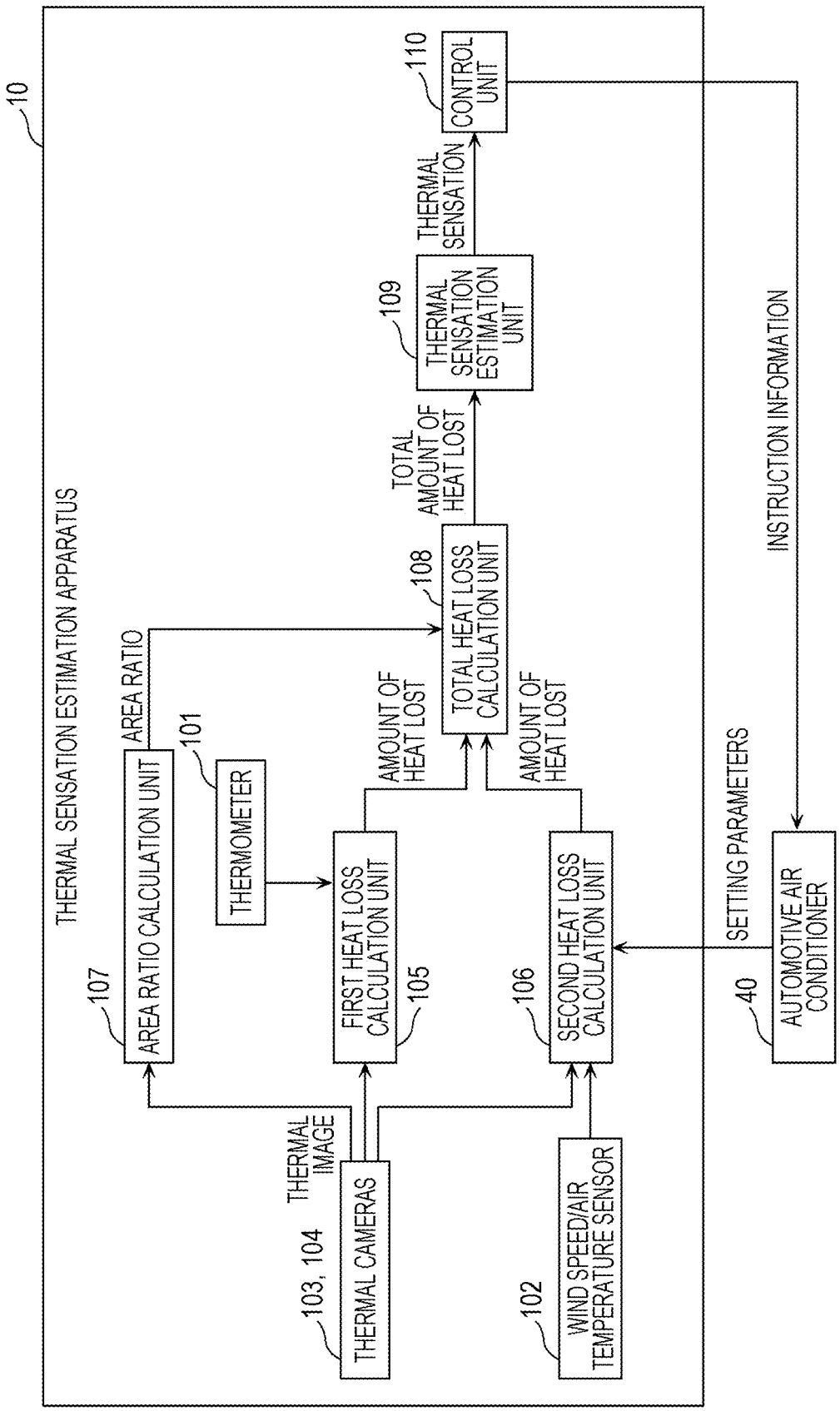
FIG. 2 is a block diagram illustrating the configuration of the thermal sensation estimation apparatus according to the first embodiment.
Figure 3:
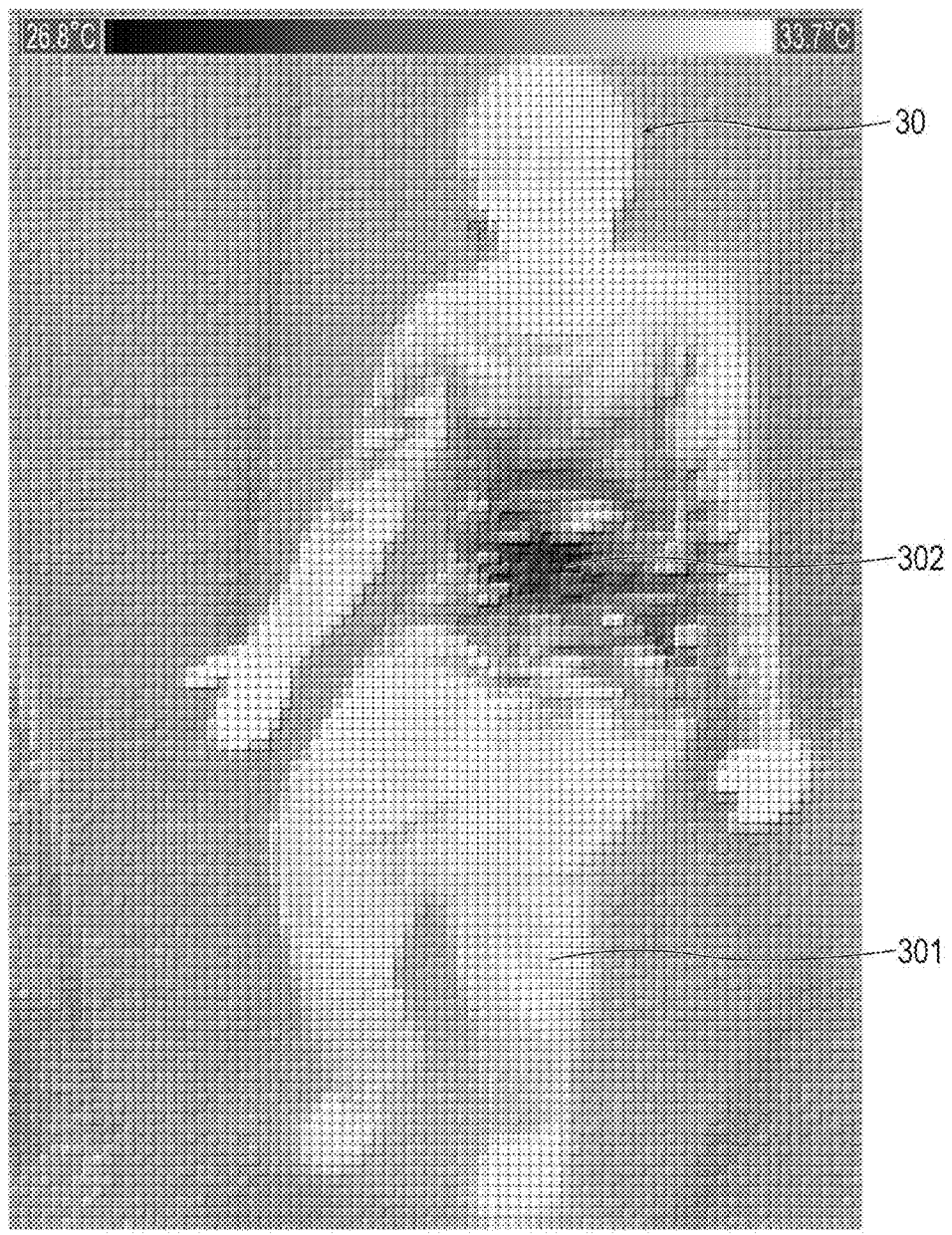
FIG. 3 is an example of a thermal image obtained by the thermal sensation estimation apparatus according to the first embodiment.

First, the configuration of a thermal sensation estimation apparatus 10 according to a first embodiment will be described with reference to FIGS. 1 to 3. FIG. 1 is a diagram illustrating a use case of the thermal sensation estimation apparatus 10 according to the first embodiment. FIG. 2 is a block diagram illustrating the configuration of the thermal sensation estimation apparatus 10 according to the first embodiment. FIG. 3 is an example of a thermal image obtained by the thermal sensation estimation apparatus 10 according to the first embodiment.

As illustrated in FIG. 1, the thermal sensation estimation apparatus 10 is installed in a vehicle body 201 of an automobile 20 (an example of a vehicle). The thermal sensation estimation apparatus 10 estimates the thermal sensation of a person 30 (a driver or the like) seated in (in contact with) a seat 202 (an example of a certain member) of the automobile 20 in a non-uniform thermal environment such as an inside of the vehicle body 201 in which, for example, a cooling operation is being performed in summer (or a heating operation is being performed in winter). The non-uniform thermal environment refers to, for example, an environment in which temperature inside the vehicle body 201 has become non-uniform because of air (cold or warm air) locally blown from an automotive air conditioner 40 installed in the vehicle body 201. As described later, the thermal sensation estimated by the thermal sensation estimation apparatus 10 is used to control any of air volume, air temperature, and wind direction of the automotive air conditioner 40. Control units of the thermal sensation estimation apparatus 10 and the automotive air conditioner 40 may be implemented as electronic control units (ECUs) and connected to a vehicle network such as a local interconnect network (LIN) or a controller area network (CAN).

As illustrated in FIG. 1, the automotive air conditioner 40 cools or heats air inside the vehicle body 201 of the automobile 20. The automotive air conditioner 40 blows cold air to an upper half of a body of the person 30 in a cooling operation and blows warm air to the upper half of the body and feet of the person 30 in a heating operation. In the present embodiment, a case will be described in which the automotive air conditioner 40 performs a cooling operation in summer. As illustrated in FIG. 2, the automotive air conditioner 40 transmits current setting parameters thereof to a second heat lost calculation unit 106 (described later) of the thermal sensation estimation apparatus 10. The setting parameters are information indicating the air volume (small or large), wind direction (feet or the upper half of the body), and air temperature (cold or warm) of the automotive air conditioner 40 and the like.

As the setting parameters of the automotive air conditioner 40, one or a plurality of pieces of information used by the automotive air conditioner 40 to set the air temperature and the air volume may be used. The plurality of pieces of information include, for example, a) the intensity of sunlight obtained by an actinometer, b) an outside temperature obtained by an outside temperature sensor, c) an inside temperature obtained by an inside temperature sensor, d) an engine coolant temperature obtained by an engine coolant temperature sensor, e) an evaporator wind temperature obtained by a thermometer at an end of an evaporator, f) an inside setting temperature input by a user, g) a blower motor voltage for controlling the wind speed of a blower, h) an air mixture door opening for controlling a mixture ratio of cool air and warm air, i) a necessary air temperature indicating a temperature of air to be blown, j) an air outlet mode indicating feet, a face, or both, and k) an air inlet mode indicating inside air or outside air.

As illustrated in FIGS. 1 and 2, the thermal sensation estimation apparatus 10 includes a thermometer 101, a wind speed/air temperature sensor 102, a first thermal camera 103, a second thermal camera 104, a first heat loss calculation unit 105, the second heat loss calculation unit 106, an area ratio calculation unit 107, a total heat loss calculation unit 108, a thermal sensation estimation unit 109, and a control unit 110.

The thermometer 101 is provided at an air intake port (an example of a certain position around the person 30) of the automotive air conditioner 40 and measures a temperature inside the vehicle body 201 (an example of a temperature around the person 30).

The wind speed/air temperature sensor 102 measures a wind speed and an air temperature around a position (e.g., an abdomen of the person 30) at which the person 30 is blown by air from the automotive air conditioner 40. For example, the wind speed/air temperature sensor 102 measures a wind speed and an air temperature for each pattern of the setting parameters of the automotive air conditioner 40 before the automobile 20 is shipped. The wind speed/air temperature sensor 102 transmits the measured wind speed and air temperature to the second heat loss calculation unit 106, in which the measured wind speed and air temperature are stored.

The first thermal camera 103 and the second thermal camera 104 detect infrared light radiated from objects and capture thermal images indicating thermal distribution in space. The first thermal camera 103 and the second thermal camera 104 are provided at different positions in the vehicle body 201. More specifically, as illustrated in FIG. 1, the first thermal camera 103 is mounted on a dashboard of the vehicle body 201, for example, and captures a thermal image (an example of a first thermal image) of a lower half of the body of the person 30 in the seat 202 from the front. The second thermal camera 104 is mounted on a rearview mirror of the vehicle body 201, for example, and captures a thermal image (an example of second thermal image) of the upper half of the body of the person 30 in the seat 202 from the front.

As illustrated in FIG. 3, the first thermal camera 103 and the second thermal camera 104 obtain a thermal image of an area including a whole body of the person 30 viewed from the front by combining a thermal image of the lower half of the body of the person 30 and a thermal image of the upper half of the body of the person 30 viewed from the front. In the thermal image illustrated in FIG. 3, the automotive air conditioner 40 blows cold air to the abdomen of the person 30. A decrease in the temperature of the abdomen of the person 30 is represented by changes in color.

In the following description, a part of a human body surface area, which includes skin and clothes of the person 30, in a thermal image not exposed to air from the automotive air conditioner 40 (exposed to a first thermal environment) will be referred to as a windless area 301 (an example of a first area). On the other hand, a part of a human body surface area in a thermal image exposed to air from the automotive air conditioner 40 (exposed to a second thermal environment different from the first thermal environment) will be referred to as a wind area 302 (an example of a second area). In the thermal image illustrated in FIG. 3, the wind area 302 is the abdomen of the person 30 and identified from the second thermal image. The windless area 301 is a part other than the abdomen of the person 30 and identified from the first and second thermal images.

The first heat loss calculation unit 105 calculates the amount of heat convected in the windless area 301 (an example of a first amount of heat lost), which is the amount of heat lost from the windless area 301 of the person 30 in a unit area. The first heat loss calculation unit 105 also calculates the total amount of heat radiated, which is the amount of heat lost from the whole body (the windless area 301 and the wind area 302) of person 30 in a unit area.

The amount of heat convected in the windless area 301 is the amount of heat lost through convection between air and the person 30 in the windless area 301. The amount of heat convected in the windless area 301 is calculated by a calculation method in which a difference between an average surface temperature of the person 30 in the windless area 301 (an average surface temperature of a part of a human body surface area exposed to the first thermal environment; an example of a first temperature) and a temperature inside the vehicle body 201 (an example of first information indicating thermal characteristics of the first thermal environment) is multiplied by a convective heat transfer coefficient (an example of a certain value) under windless conditions. The average surface temperature of the person 30 in the windless area 301 is obtained from thermal images captured by the first thermal camera 103 and the second thermal camera 104. The temperature inside the vehicle body 201 is, for example, measured by the thermometer 101. Alternatively, an average temperature of a background image, which is a part of a thermal image other than the person 30, may be used as the temperature inside the vehicle body 201. The convective heat transfer coefficient under windless conditions is a fixed value set in advance.

The total amount of heat radiated is calculated by a calculation method in which a difference between an average radiation temperature (an example of the first information) around the person 30 and an average surface temperature of the whole body of the person 30 is multiplied by a radiative heat transfer coefficient. The average radiation temperature and the average surface temperature of the whole body of the person 30 are obtained from thermal images captured by the first thermal camera 103 and the second thermal camera 104. Alternatively, an average temperature of a background image, which is a part of a thermal image other than the person 30, may be used as the average radiation temperature. Alternatively, the average radiation temperature may be obtained by a globe thermometer (not illustrated) provided in the vehicle body 201. The radiative heat transfer coefficient is a fixed value set in advance.

The second heat loss calculation unit 106 calculates the amount of heat convected in the wind area 302 (an example of a second amount of heat lost), which is the amount of heat lost from the wind area 302 of the person 30 in a unit area. The amount of heat convected in the wind area 302 is the amount of heat lost through convection between air and the person 30 in the wind area 302. The amount of heat convected in the wind area 302 is calculated by a calculation method in which a difference between an average surface temperature of the person 30 in the wind area 302 (an average surface temperature of a part of a human body surface area exposed to the second thermal environment; an example of a second temperature) and an air temperature (an example of second information indicating thermal characteristics of the second thermal environment) is multiplied by a convective heat transfer coefficient (an example of a certain value) during air conditioning. The average surface temperature of the person 30 in the wind area 302 is obtained from thermal images captured by the first thermal camera 103 and the second thermal camera 104. After the person 30 is seated in the seat 202 of the automobile 20 and the automotive air conditioner 40 begins to operate, the second heat loss calculation unit 106 reads the setting parameters of the automotive air conditioner 40 and a wind speed and an air temperature corresponding to the setting parameters. Alternatively, the second heat loss calculation unit 106 may estimate the wind speed and the air temperature by identifying a position of the person 30 in the vehicle body 201 using the setting parameters and thermal images.

The second heat loss calculation unit 106 sets the convective heat transfer coefficient during air conditioning on the basis of the read wind speed (an example of the second information). Alternatively, the second heat loss calculation unit 106 may store in advance a table in which wind speed and the convective heat transfer coefficient are associated with each other, for example, and read a convective heat transfer coefficient during air conditioning corresponding to the wind speed.

In general, the person 30 loses heat to the outside through a) convection (includes conduction), b) radiation, and c) expiration and the evaporation of perspiration. Expiration and the evaporation of perspiration remain constant when the person 30 is at rest. The first heat loss calculation unit 105 and the second heat loss calculation unit 106, therefore, as described above, calculate the amount of heat lost through convection and the amount of heat lost through radiation, which are dominant factors in determining thermal sensation. Specific calculation methods used by the first heat loss calculation unit 105 and the second heat loss calculation unit 106 will be described later.

The area ratio calculation unit 107 calculates a ratio of an area of the wind area 302 of the person 30 in thermal images captured by the first thermal camera 103 and the second thermal camera 104 to an area of the whole body (the windless area 301 and the wind area 302) of the person 30. Because the area of the wind area 302 can be calculated on the basis of the wind direction and a wind range of the automotive air conditioner 40, the area of the wind area 302 may be measured in advance, for example, before the automobile 20 is shipped. Since the area of the whole body of the person 30 varies depending on physical features of the person 30, the area of the whole body of the person 30 is calculated from thermal images each time the automotive air conditioner 40 begins to operate. Alternatively, if a temperature histogram of a human body surface area of thermal images is obtained, for example, a peak of the wind area 302 at which temperature drops and a peak of the windless area 301 at which temperature does not drop are observed. The area ratio calculation unit 107 may calculate the ratio of the area of the wind area 302 of the person 30 to the area of the whole body of the person 30 on the basis of areas of these peaks. Alternatively, the area ratio calculation unit 107 may use a preset value as the ratio.

The total heat loss calculation unit 108 calculates the total amount of heat convected by weight-averaging the amount of heat convected in the windless area 301 calculated by the first heat loss calculation unit 105 and the amount of heat convected in the wind area 302 calculated by the second heat loss calculation unit 106 using the ratio calculated by the area ratio calculation unit 107. The total amount of heat convected refers to the amount of heat lost from the whole body (the windless area 301 and the wind area 302) of the person 30 in a unit area. The total heat loss calculation unit 108 also calculates the total amount of heat lost by adding the total amount of heat convected and the total amount of heat radiated calculated by the first heat loss calculation unit 105 and multiplying a result of the addition by a certain area ratio. The total amount of heat lost is the amount of heat lost from the whole body of the person 30 in a unit area. A specific calculation method used by the total heat loss calculation unit 108 will be described later.

The thermal sensation estimation unit 109 estimates the thermal sensation of the person 30 on the basis of the total amount of heat lost calculated by the total heat loss calculation unit 108. A specific estimation method used by the thermal sensation estimation unit 109 will be described later.

The control unit 110 transmits (outputs), to the automotive air conditioner 40, instruction information for controlling at least one of the air volume, air temperature, and wind direction of the automotive air conditioner 40 on the basis of thermal sensation estimated by the thermal sensation estimation unit 109. Setting parameters of the automotive air conditioner 40 controlled on the basis of a thermal sensation include a) the blower motor voltage for controlling the wind speed of the blower, b) the air mixture door opening for controlling the mixture ratio of cool air and warm air, c) the necessary air temperature indicating the temperature of air to be blown, d) the air outlet mode indicating feet, a face, or both, and k) the air inlet mode indicating inside air or outside air. The evaporator temperature and the engine coolant temperature may also be controlled, if possible.

Some or all of the first heat loss calculation unit 105, the second heat loss calculation unit 106, the area ratio calculation unit 107, the total heat loss calculation unit 108, the thermal sensation estimation unit 109, and the control unit 110 may be achieved as software by a processor (not illustrated), which is included in the thermal sensation estimation apparatus 10, that executes a program, or may be achieved as hardware by a dedicated circuit. Information used by the above components for their respective processes is stored in a memory (not illustrated) or a storage (not illustrated) included in the thermal sensation estimation apparatus 10.

1-2. Operation of Thermal Sensation Estimation Apparatus

Figure 4:
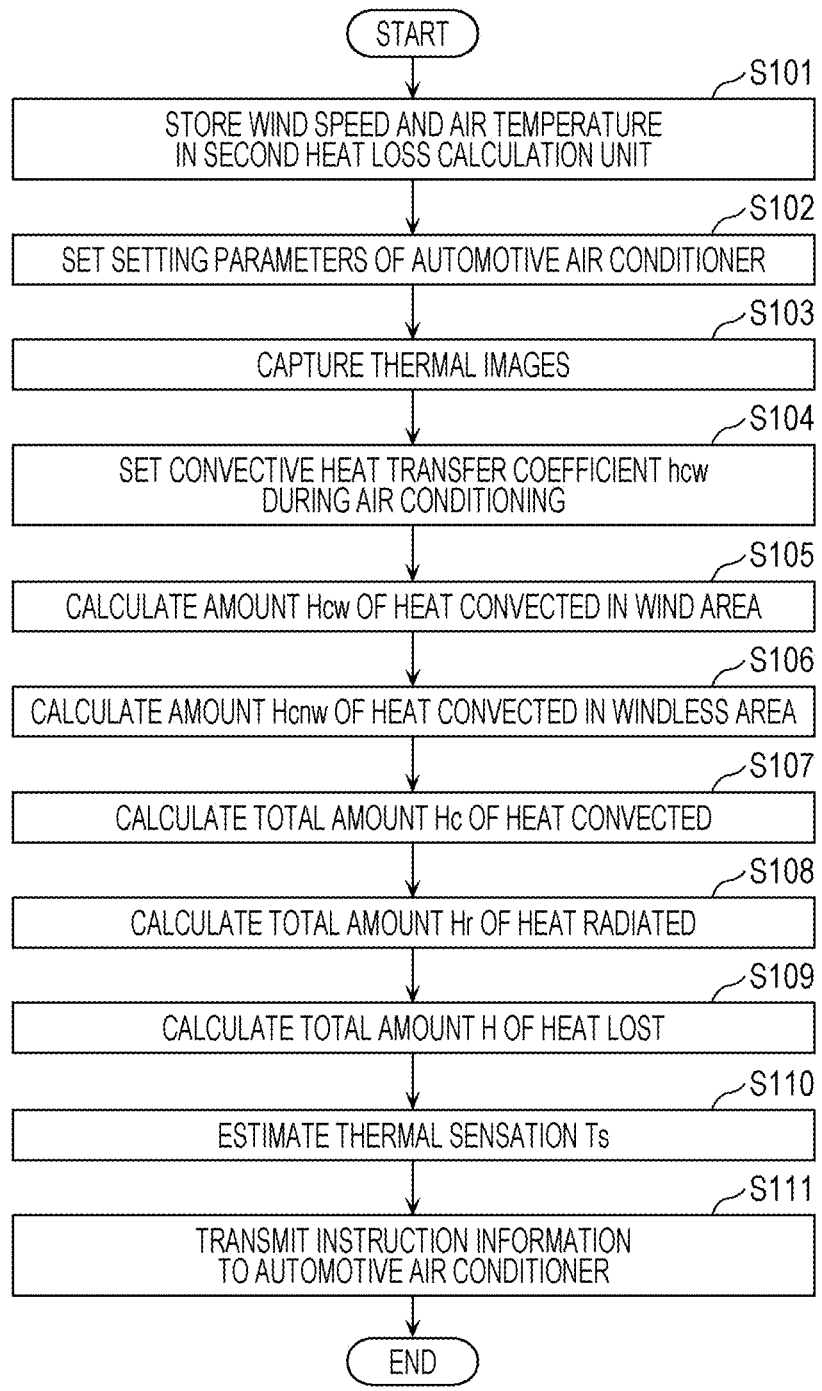
FIG. 4 is a flowchart illustrating a procedure of the operation of the thermal sensation estimation apparatus according to the first embodiment.

Next, the operation (the method for estimating thermal sensation) of the thermal sensation estimation apparatus 10 according to the first embodiment will be described with reference to FIG. 4. FIG. 4 is a flowchart illustrating a procedure of the operation of the thermal sensation estimation apparatus 10 according to the first embodiment.

As illustrated in FIG. 4, first, before the automobile 20 is shipped, for example, the wind speed/air temperature sensor 102 measures the wind speed and the air temperature of the automotive air conditioner 40 for each pattern of the setting parameters of the automotive air conditioner 40 and stores the measured wind speed and air temperature in the second heat loss calculation unit 106 (S101).

After the person 30 gets in the automobile 20 and the automotive air conditioner 40 begins to operate, the setting parameters of the automotive air conditioner 40 are set (S102).

The first thermal camera 103 and the second thermal camera 104 then capture thermal images of the whole body of the person 30 from the front (S103).

The second heat loss calculation unit 106 then reads a wind speed corresponding to the setting parameters set in step S102 and sets a convective heat transfer coefficient hcw during air conditioning on the basis of the read wind speed (S104).

The second heat loss calculation unit 106 then obtains an average surface temperature Tcw in the wind area 302 on the basis of the thermal images captured in step S103. The second heat loss calculation unit 106 also reads an air temperature Tw corresponding to the setting parameters set in step S102. The second heat loss calculation unit 106 calculates an amount Hcw of heat convected in the wind area 302 using a calculation method in which a difference between the average surface temperature Tcw in the wind area 302 and the air temperature Tw is multiplied by the convective heat transfer coefficient hcw during air conditioning as in expression (1) (S105).

$$Hcw = hcw \times (Tcw - Tw) \quad (1)$$

Hcw: Amount of heat convected in wind area
hcw: Convective heat transfer coefficient during air conditioning
Tw: Air temperature
Tcw: Average surface temperature in wind area The first heat loss calculation unit 105 then obtains an average surface temperature Tcnw in the windless area 301 on the basis of the thermal images captured in step S103. The first heat loss calculation unit 105 also obtains a temperature Ta inside the vehicle body 201 measured by the thermometer 101. The first heat loss calculation unit 105 calculates an amount Hcnw of heat convected in the windless area 301 using a calculation method in which a difference between the average surface temperature Tcnw in the windless area 301 and the temperature Ta is multiplied by a convective heat transfer coefficient hcnw under windless conditions as in expression (2) (S106).

$$Hcnw = hcnw \times (Tcnw - Ta) \quad (2)$$

Hcnw: Amount of heat convected in windless area
hcnw: Convective heat transfer coefficient under windless conditions
Ta: Temperature
Tcnw: Average surface temperature in windless area The area ratio calculation unit 107 then calculates a ratio Ww (=Wa/Wt) of an area Wa of the wind area 302 of the person 30 to an area Wt of the whole body of the person 30 on the basis of the thermal images captured in step S103. The total heat loss calculation unit 108 then calculates a total amount Hc of heat convected by weight-averaging the amount Hcw of heat convected in the wind area 302 and the amount Hcnw of heat convected in the windless area 301 using the ratio Ww (S107).

$$Hc = Ww \times Hcw + (1 - Ww) \times Hcnw \quad (3)$$

Hc: Total amount of heat convected
Ww: Ratio of area of wind area to area of whole body The first heat loss calculation unit 105 then obtains an average radiation temperature Tr and an average surface temperature Tc of the whole body on the basis of the thermal images captured in step S103. The first heat loss calculation unit 105 calculates a total amount Hr of heat radiated using a calculation method in which a difference between the average surface temperature Tc of the whole body and the average radiation temperature Tr is multiplied by the radiative heat transfer coefficient hr as in expression (4) (S108).

$$Hr = hr \times (Tc - Tr) \quad (4)$$

Hr: Total amount of heat radiated
hr: Radiative heat transfer coefficient
Tc: Average surface temperature of whole body
Tr: Average radiation temperature The total heat loss calculation unit 108 then adds the total amount Hc of heat convected and the total amount Hr of heat radiated as in expression (5). The total heat loss calculation unit 108 also calculates a total amount H of heat lost by multiplying a result of the addition by 1−Ws, which is a ratio (Wb/Wt) of an area Wb of an insulated part 303 of the person 30 (a part of the person 30 insulated by the seat 202) to the area Wt of the whole body of the person 30, as in expression (5) (S109).

$$H = (Hc + Hr) \times (1 - Ws) \quad (3)$$

H: Total amount of heat lost
Ws: Ratio of area of insulated part 303 to area of whole body The thermal sensation estimation unit 109 then estimates a thermal sensation Ts on the basis of the total amount H of heat lost as in expression (6) (S110). The thermal sensation Ts ranges, for example, from "−4" (cold) to "+4" (hot). A central value "0" (neutral) of the thermal sensation Ts1 indicates a comfortable state.

$$Ts = a \times H + b \quad (6)$$

Ts: Thermal sensation
a: Coefficient
b: Y-intercept

The control unit 110 then transmits instruction information to the automotive air conditioner 40 on the basis of the estimated thermal sensation Ts (S111). As a result, at least one of the air volume, air temperature, and wind direction of the automotive air conditioner 40 is controlled such that, for example, the thermal sensation Ts becomes close to the value (neutral value) at which the person 30 does not feel cold or hot.

1-3. Advantageous Effects

As described above, when a part of a human body surface area is exposed to air from the automotive air conditioner 40, for example, the thermal sensation estimation apparatus 10 according to the present embodiment calculates the amount of heat lost in the wind area 302 and the amount of heat lost in the windless area 301 and then calculates the total amount of heats lost by combining the amount of heat lost in the wind area 302 and the amount of heat lost in the windless area 301 using an area ratio. The thermal sensation estimation apparatus 10 then estimates thermal sensation on the basis of the total amount of heat lost calculated in this manner. That is, since the thermal sensation estimation apparatus 10 calculates the total amount of heat lost in consideration of the human body surface area exposed to a non-uniform thermal environment, the thermal sensation estimation apparatus 10 can accurately estimate thermal sensation even if the person 30 is in a non-uniform thermal environment.

By installing the thermal sensation estimation apparatus 10 in the automobile 20, for example, the automotive air conditioner 40 can be controlled such that the thermal sensation becomes close to a value at which the person 30 does not feel cold or hot. As a result, the automotive air conditioner 40 does not cool or heat too much, and power is saved. The power that would otherwise be consumed by the automotive air conditioner 40, therefore, can be used to drive the automobile 20, and the automobile 20 can travel a longer distance.

Furthermore, since the thermal sensation estimation apparatus 10 according to the present embodiment estimates thermal sensation on the basis of the total amount of heat lost from the whole body of the person 30 in a unit area, the thermal sensation estimation apparatus 10 can estimate thermal sensation that does not depend on the physical features of the person 30.

Second Embodiment 2-1. Configuration of Thermal Sensation Estimation Apparatus

Figure 5:
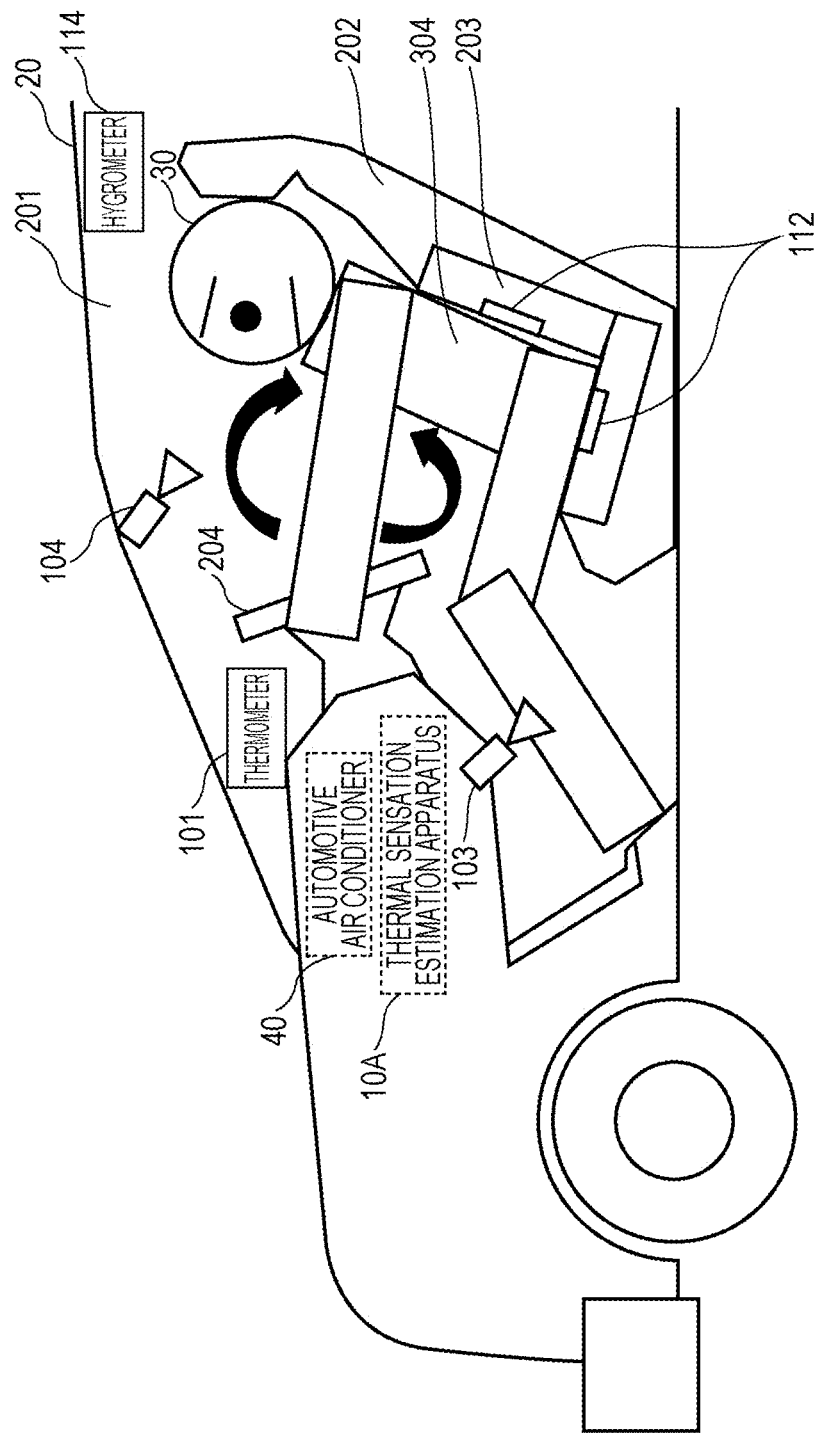
FIG. 5 is a diagram illustrating a use case of a thermal sensation estimation apparatus according to a second embodiment.
Figure 6:
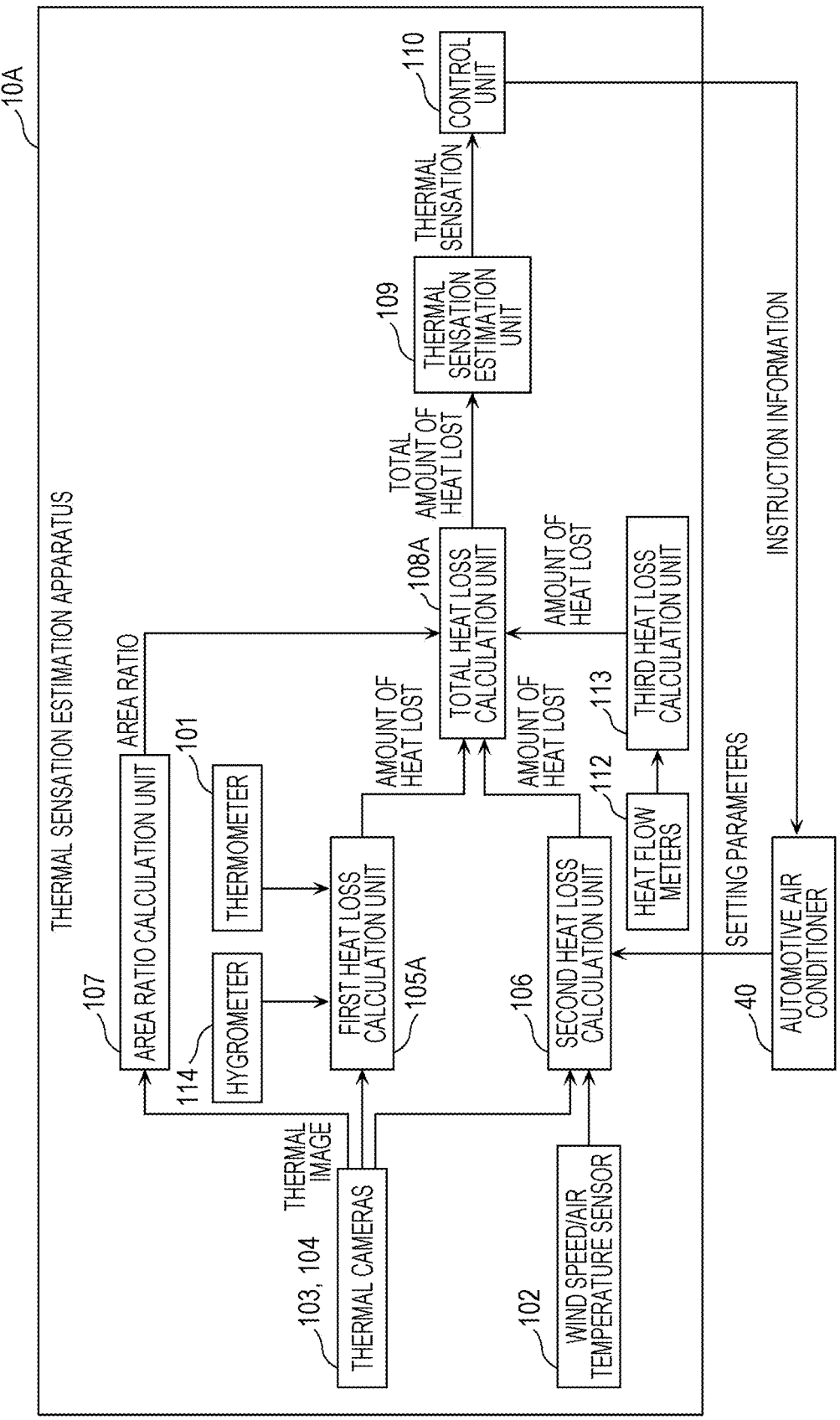
FIG. 6 is a block diagram illustrating the configuration of the thermal sensation estimation apparatus according to the second embodiment.

Next, the configuration of a thermal sensation estimation apparatus 10A according to a second embodiment will be described with reference to FIGS. 5 and 6. FIG. 5 is a diagram illustrating a use case of the thermal sensation estimation apparatus 10A according to the second embodiment. FIG. 6 is a block diagram illustrating the configuration of the thermal sensation estimation apparatus 10A according to the second embodiment. In the present embodiment, the same components as those according to the first embodiment are given the same reference numerals, and description thereof is omitted.

In the present embodiment, a case will be described in which the automotive air conditioner 40 performs a heating operation in winter. As illustrated in FIG. 5, seat heaters 203 for heating a back of the person 30 are provided in the seat 202 of the automobile 20.

As illustrated in FIGS. 5 and 6, the thermal sensation estimation apparatus 10A includes heat flow meters 112, a third heat loss calculation unit 113, and a hygrometer 114 in addition to the components described in the first embodiment.

As illustrated in FIG. 5, the heat flow meters 112 are provided on the seat heaters 203 and measure the amount of heat transferred from the seat heaters 203 to the person 30 (an example of the amount of heat transferred between the seat 202 and the person 30). Alternatively, the heat flow meters 112 may measure the amount of heat that the seat heaters 203 receive from the person 30 (an example of the amount of heat transferred between the seat 202 and the person 30).

The third heat loss calculation unit 113 calculates the amount of heat conducted (an example of a third amount of heat lost) in a seat part 304 (an example of a third area), in which the person 30 is in contact with the seat heaters 203, of the human body area. More specifically, the third heat loss calculation unit 113 calculates a reciprocal of the amount of heat transferred from the seat heaters 203 to the person 30 measured by the heat flow meters 112 as the amount of heat conducted in the seat part 304.

Although the third heat loss calculation unit 113 calculates the amount of heat conducted using the heat flow meters 112 in the present embodiment, the components used by the third heat loss calculation unit 113 to calculate the amount of heat conducted are not limited to this. For example, thermometers (not illustrated) may be provided on the seat heaters 203 instead of the heat flow meters 112. In this case, the third heat loss calculation unit 113 calculates the amount of heat conducted on the basis of temperatures calculated by the thermometers. Alternatively, the heat flow meters 112 may be omitted. In this case, the third heat loss calculation unit 113 calculates (estimates) the amount of heat conducted on the basis of power (current) supplied to the seat heaters 203.

The hygrometer 114 is provided inside the vehicle body 201 of the automobile 20 and measures a humidity (an example of a thermal environment) inside the vehicle body 201. The hygrometer 114 transmits humidity information regarding the measured humidity to a first heat loss calculation unit 105A. The first heat loss calculation unit 105A corrects the convective heat transfer coefficient hcnw under windless conditions in accordance with the received humidity information.

The third heat loss calculation unit 113 may be achieved as software by a processor (not illustrated), which is included in the thermal sensation estimation apparatus 10A, that executes a program, or may be achieved as hardware by a dedicated circuit. Information used by the third heat loss calculation unit 113 to perform a process is stored in a memory (not illustrated) or a storage (not illustrated) included in the thermal sensation estimation apparatus 10A.

2-2. Operation of Thermal Sensation Estimation Apparatus

Next, the operation (the method for estimating thermal sensation) of the thermal sensation estimation apparatus 10A according to the second embodiment will be described with reference to FIG. 7. FIG. 7 is a flowchart illustrating a procedure of the operation of the thermal sensation estimation apparatus 10A according to the second embodiment. In FIG. 7, the same steps as those according to the first embodiment illustrated in FIG. 4 are given the same reference numerals, and description thereof is omitted.

First, as in the first embodiment, steps S101 to S105 are performed. The first heat loss calculation unit 105A then corrects the convective heat transfer coefficient hcnw under windless conditions in accordance with humidity information from the hygrometer 114 to obtain a convective heat transfer coefficient hcnw' under windless conditions (S201).

The first heat loss calculation unit 105A then calculates the amount Hcnw of heat convected in the windless area 301 based on the humidity using a calculation method in which the difference between the average surface temperature Tcnw in the windless area 301 (refer to FIG. 3) and the temperature Ta is multiplied by the convective heat transfer coefficient hcnw' under windless conditions as in expression (7) (S202).

$$Hcnw = hcnw' \times (Tcnw - Ta) \quad (7)$$

Hcnw: Amount of heat convected in windless area based on humidity
hcnw': Convective heat transfer coefficient under windless conditions
Ta: Temperature
Tcnw: Average surface temperature in windless area Steps S107 and S108 are then performed as in the first embodiment. The third heat loss calculation unit 113 then calculates the reciprocal of the amount of heat transferred from the seat heaters 203 to the person 30 measured by the heat flow meters 112 as the amount Hcd of heat conducted in the seat part 304 (S203).

A total heat loss calculation unit 108A then calculates the total amount H of heat lost by weight-averaging the total amount Hc of heat convected, the total amount Hr of heat radiated, and the amount Hcd of heat conducted using an area ratio Wst as in expression (8) (S204).

$$H=(Hc+Hr)\times(1-Wst)+Wst\times Hcd \quad (8)$$

H: Total amount of heat lost
Wst: Ratio of area of seat part 304 to area of whole body
Hcd: Amount of heat conducted Steps S110 and S111 are then performed as in the first embodiment.

2-3. Advantageous Effects

As described above, the thermal sensation estimation apparatus 10A according to the present embodiment calculates the amount of heat lost in the wind area 302 (refer to FIG. 3) and the amount of heat lost in the windless area 301, calculates the reciprocal of the amount of heat transferred from the seat heaters 203 to the person 30 as the amount Hcd of heat conducted in the seat part 304, and calculates the total amount of heat lost by combining these using an area ratio. As a result, thermal sensation can be accurately estimated as in the first embodiment even in a non-uniform thermal environment in which, for example, the automotive air conditioner 40 and the seat heaters 203 heat the air inside the vehicle body 201 in winter.

Modifications

Although the method for estimating thermal sensation and the like according to one or a plurality of aspects have been described on the basis of the first and second embodiments, the present disclosure is not limited to the first and second embodiments. The one or plurality of aspects may also include modes obtained by modifying the first or second embodiment in various ways conceivable by those skilled in the art and modes constructed by combining different components in the first and second embodiments insofar as the scope of the present disclosure is not deviated from. For example, the first and second embodiments may be combined with each other.

Although the seat heaters 203 for heating the back of the person 30 are provided in the seat 202 in the second embodiment, for example, a steering wheel heater for heating hands of the person 30 may be provided in a steering wheel 204 (refer to FIG. 5), instead. In this case, the steering wheel 204 is provided with a heat flow meter or a thermometer for measuring the amount of heat transferred between the steering wheel 204 and the person 30. In this case, too, the amount of heat lost can be calculated using the same method as above.

Although the air conditioner is the automotive air conditioner 40 in the above embodiments, for example, the air conditioner may be a spot air conditioner installed in a room, instead.

Although the vehicle is the automobile 20 in the above embodiments, for example, the vehicle may be a train, an airplane, or the like, instead.

Although the thermal sensation estimation apparatus 10 (10A) is installed in the automobile 20 in the above embodiments, for example, the thermal sensation estimation apparatus 10 (10A) may be installed in a room of a house, instead.

Some or all of the components of the apparatuses may be achieved by an integrated circuit (IC) card or a separate module removably attached to the apparatuses. The IC card or the module is a computer system including a microprocessor, a read-only memory (ROM), and a random-access memory (RAM). The IC card or the module may include a super-multifunctional large-scale integration (LSI) circuit. When the microprocessor operates in accordance with a computer program, the IC card or the module achieves functions thereof. The IC card or the module may be tamper-resistant.

The present disclosure may be the above-described methods. The present disclosure may be a computer program that achieves these methods using a computer, or may be a digital signal including the computer program. The present disclosure may be a computer-readable recording medium storing the computer program or the digital signal, such as a flexible disk, a hard disk, a CD-ROM, a magneto-optical (MO) disk, a digital versatile disc (DVD), a DVD-ROM, a DVD-RAM, a Blu-ray Disc (BD; registered trademark), or a semiconductor memory. The present disclosure may be the digital signal stored in the recording medium. The present disclosure may be the computer program or the digital signal transferred through an electrical communication line, a wireless or wired communication line, a network typified by the Internet, datacasting, or the like. The present disclosure may be a computer system including a microprocessor and a memory. The memory may store the computer program, and the microprocessor may operate in accordance with the computer program. The present disclosure may be implemented by another independent computer system by transferring the program or the digital signal stored in the recording medium or by transferring the program or the digital signal through the network or the like.

The present disclosure can be used, for example, for a method for estimating thermal sensation.

What is claimed is:

1. A method used by a thermal sensation estimation apparatus, the method comprising:
    obtaining a thermal image of an area including a person captured by a thermal camera;
    calculating, on the basis of the thermal image, a first temperature, which is a surface temperature of a first area, which is a part of a human body surface area including skin or clothes of the person, exposed to a first thermal environment, and a second temperature, which is a surface temperature of a second area, which is at least a part of the human body surface area other than the first area, exposed to a second thermal environment different from the first thermal environment;
    calculating a first amount of heat lost, which is an amount of heat lost from the first area of the person in a unit area, on the basis of the first temperature and first information indicating thermal characteristics of the first thermal environment;
    calculating a second amount of heat lost, which is an amount of heat lost from the second area of the person in a unit area, on the basis of the second temperature and second information indicating thermal characteristics of the second thermal environment;
    obtaining an area ratio of the first area to the second area;
    calculating a total amount of heat lost, which is an amount of heat lost from a whole body of the person in a unit area, on the basis of the first amount of heat lost, the second amount of heat lost, and the area ratio; and
    estimating thermal sensation, which indicates a degree of warmth or coldness of the person, on the basis of the total amount of heat lost.

2. The method according to claim 1,
    wherein the first area includes at least a part of the human body surface area not exposed to air from an air conditioner, and
    wherein the second area includes at least a part of the human body surface area exposed to the air from the air conditioner.

3. The method according to claim 1,
wherein the total amount of heat lost is calculated by weight-averaging the first amount of heat lost and the second amount of heat lost using the area ratio.

4. The method according to claim 1,
wherein the area ratio is calculated on the basis of an area of the first area and an area of the second area in the thermal image.

5. The method according to claim 1,
wherein the area ratio is calculated on the basis of a temperature histogram of the thermal image.

6. The method according to claim 1,
wherein the area ratio is a preset value.

7. The method according to claim 1,
wherein the thermal camera includes a first thermal camera provided at a certain position and a second thermal camera provided at a position different from that of the first thermal camera,
wherein the thermal image includes a first thermal image captured by the first thermal camera and a second thermal image captured by the second thermal camera,
wherein the first area is identified from the first thermal image, and
wherein the second area is identified from the second thermal image.

8. The method according claim 1,
wherein the person is in contact with a certain member,
wherein an amount of heat transferred between the person and the certain member in a third area, which is a part of the human body surface area in which the person is in contact with the certain member, is calculated on the basis of an amount of heat received by or lost from the certain member,
wherein an area ratio of the first area, the second area, and the third area is obtained, and
wherein the total amount of heat lost is calculated on the basis of the first amount of heat lost, the second amount of heat lost, the amount of heat transferred, and the area ratio.

9. The method according to claim 8,
wherein the certain member is at least either a seat of a vehicle in which the person stays or a steering wheel, and
wherein the amount of heat transferred is an amount of heat transferred on a surface of the person's body at which the person is in contact with at least either the seat or the handle.

10. The method according to claim 9,
wherein the amount of heat transferred is measured by a thermometer provided for at least either the seat or the steering wheel.

11. The method according to claim 9,
wherein the amount of heat transferred is measured by a heat flow meter provided for at least either the seat or the steering wheel.

12. The method according to claim 1,
wherein at least either the first information or the second information includes a temperature around the person.

13. The method according to claim 12,
wherein at least either the first amount of heat lost or the second amount of heat lost is calculated by a calculation method in which a difference between the first temperature or the second temperature, whichever corresponds to the amount of heat lost, and the temperature is multiplied by a certain value.

14. The method according to claim 12,
wherein the temperature is calculated on the basis of a thermal image representing temperature distribution in space.

15. The method according to claim 12,
wherein the temperature is measured by a thermometer provided at a certain position around the person.

16. The method according to claim 1,
wherein at least either the first information or the second information includes radiation temperature.

17. The method according to claim 16,
wherein the radiation temperature is calculated on the basis of a thermal image representing temperature distribution in space.

18. The method according to claim 1,
wherein at least either the first information or the second information includes wind speed and air temperature of wind around the person.

19. The method according to claim 18,
wherein a convective heat transfer coefficient between the human body surface area and at least either the first thermal environment or the second thermal environment is set in accordance with the wind speed, and
wherein at least either the first amount of heat lost or the second amount of heat lost is calculated on the basis of the convective heat transfer coefficient, the air temperature, and the first temperature or the second temperature, whichever corresponds to the amount of heat lost.

20. The method according to claim 19,
wherein at least either the first amount of heat lost or the second amount of heat lost is calculated by a calculation method in which a difference between the first temperature or the second temperature, whichever corresponds to the amount of heat lost, and the air temperature is multiplied by the convective heat transfer coefficient.

21. The method according to claim 19,
wherein the wind speed and the air temperature are wind speed and air temperature of air from an air conditioner installed in space where the person stays.

22. The method according to claim 21, further comprising:
obtaining setting parameters of the air conditioner; and
calculating at least either the first amount of heat lost or the second amount of heat lost using the wind speed and the air temperature set using the setting parameters.

23. The method according to claim 22, further comprising:
measuring in advance the wind speed and the air temperature at each position in the space for each pattern of the setting parameters of the air conditioner;
estimating the wind speed and the air temperature in the human body surface area by identifying a position of the person in the space using the setting parameters of the air conditioner and the thermal image; and
calculating at least either the first amount of heat lost and the second amount of heat lost using the estimated wind speed and air temperature.

24. The method according to claim 1,
wherein the first thermal environment and the second thermal environment include humidity around the person.

25. The method according to claim 1, further comprising:
outputting, to an air conditioner, instruction information for controlling air volume, air temperature, or wind direction of the air conditioner in accordance with the estimated thermal sensation.

26. The method according to claim 1,
wherein the thermal image is captured inside a vehicle body of a vehicle in which the person stays.

27. A thermal sensation estimation apparatus comprising:
a processor; and
a memory,
wherein the processor performs operations including
obtaining a thermal image of an area including a person captured by a thermal camera,
calculating, on the basis of the thermal image, a first temperature, which is a surface temperature of a first area, which is a part of a human body surface area including skin or clothes of the person, exposed to a first thermal environment, and a second temperature, which is a surface temperature of a second area, which is at least a part of the human body surface area other than the first area, exposed to a second thermal environment different from the first thermal environment,
calculating a first amount of heat lost, which is an amount of heat lost from the first area of the person in a unit area, on the basis of the first temperature and first information indicating thermal characteristics of the first thermal environment,
calculating a second amount of heat lost, which is an amount of heat lost from the second area of the person in a unit area, on the basis of the second temperature and second information indicating thermal characteristics of the second thermal environment,
obtaining an area ratio of the first area to the second area,
calculating a total amount of heat lost, which is an amount of heat lost from a whole body of the person in a unit area, on the basis of the first amount of heat lost, the second amount of heat lost, and the area ratio, and
estimating thermal sensation, which indicates a degree of warmth or coldness of the person, on the basis of the total amount of heat lost.

28. An air conditioner comprising:
the thermal sensation estimation apparatus according to claim 27,
wherein air volume, air temperature, or wind direction is controlled on the basis of the thermal sensation estimated by the thermal sensation estimation apparatus.

29. A non-transitory recording medium storing a program for causing a computer to function as a thermal sensation estimation apparatus, the program causing the computer to perform operations comprising:
obtaining a thermal image of an area including a person captured by a thermal camera;
calculating, on the basis of the thermal image, a first temperature, which is a surface temperature of a first area, which is a part of a human body surface area including skin or clothes of the person, exposed to a first thermal environment, and a second temperature, which is a surface temperature of a second area, which is at least a part of the human body surface area other than the first area, exposed to a second thermal environment different from the first thermal environment;
calculating a first amount of heat lost, which is an amount of heat lost from the first area of the person in a unit area, on the basis of the first temperature and first information indicating thermal characteristics of the first thermal environment;
calculating a second amount of heat lost, which is an amount of heat lost from the second area of the person in a unit area, on the basis of the second temperature and second information indicating thermal characteristics of the second thermal environment;
obtaining an area ratio of the first area to the second area;
calculating a total amount of heat lost, which is an amount of heat lost from a whole body of the person in a unit area, on the basis of the first amount of heat lost, the second amount of heat lost, and the area ratio; and
estimating thermal sensation, which indicates a degree of warmth or coldness of the person, on the basis of the total amount of heat lost.

* * * * *